United States Patent [19]
Portillo, Jr.

[11] Patent Number: 5,094,748
[45] Date of Patent: Mar. 10, 1992

[54] CENTRALIZED BICARBONATE CONCENTRATE DISTRIBUTION SYSTEM

[76] Inventor: Luis C. Portillo, Jr., 1328 Blanco Rd., San Antonio, Tex. 8248

[21] Appl. No.: 681,317

[22] Filed: Apr. 4, 1991

Related U.S. Application Data

[62] Division of Ser. No. 475,645, Feb. 6, 1990, Pat. No. 5,015,389.

[51] Int. Cl.$^5$ .............................................. B01D 61/24
[52] U.S. Cl. ............................... 210/321.71; 210/541; 210/542
[58] Field of Search ................ 210/646, 321.71, 321.6, 210/321.62, 541, 542; 514/568; 424/451, 81, 686, 482, 717

[56] References Cited

U.S. PATENT DOCUMENTS

| | | |
|---|---|---|
| 3,545,438 | 12/1970 | De Vries |
| 3,799,873 | 3/1974 | Brown |
| 3,878,095 | 4/1975 | Frasier et al. |
| 4,202,764 | 5/1980 | Afflerbaugh et al. |
| 4,289,750 | 9/1981 | Kopp et al. ........................ 424/451 |

OTHER PUBLICATIONS

McDonald, Harold, Jr., Replacement of Renal Function, *European Dialysis and Transplant Association*, vol. 111, 1966 at pp. 366-367.
McDonald, Harold P., Jr., An Automatic Peritoneal Dialysis Machine: Preliminary Report, *Transamerican Society for Artificial Internal Organs*, vol. XI, 1965, at pp. 83-85.
McDonald, Harold, Jr., An Automatic Peritoneal Machine for Hospital or Home-Peritoneal Dialysis: Preliminary Report, *Transamerican Society for Artificial Internal Organs*, vol. XV, 1969, at pp. 108-111.
Sheldon, S. et al., Three Years of Experience with On-Line Preparation of Sterile Pyrogen-Free Infusate for Haemofiltration, *Contr. Nephrol.*, vol. 32, 1982 at pp. 160-164.
Rindi, P. et al., Clincical Experience with a New Hemodiafiltration, *Transamerican Society for Artifical Internal Organs*, vol. XXXIV, 1988, at pp. 765-768.
Henderson, et al., Successful production of sterile pyrogen-free electrolyte solution by ultrafiltration, *Kidney International*, vol. 14, 1978, at pp. 522-525.
Ronoco, C. et al., Technical and Clinical Evaluation of a New System for Ultrafiltration Control During Hemodialysis, *Transamerican Society for Artificial Internal Organs*, vol. XXXIV, 198, at pp. 613-616.

*Primary Examiner*—Frank Sever
*Attorney, Agent, or Firm*—Cox & Smith Incorporated

[57] ABSTRACT

The present invention relates to apparatus for facilitating distribution of bicarbonate concentration for use in hemodialysis. More particularly, the present invention relates to a centralized bicarbonate concentrate circulatory system for automatically controlled distribution and recirculation of bicarbonate concentrate to service a plurality of remote hemodialysis stations while achieving necessary control of various bicarbonate concentration characteristics, including concentrations, acidity and temperature, as well as the degree of contaminants.

9 Claims, 4 Drawing Sheets

CENTRALIZED BICARBONATE CONCENTRATE DISTRIBUTION SYSTEM

This application is a divisional of co-pending application Ser. No. 07/475,645, filed on Feb. 6, 1990 now U.S. Pat. No. 5,015,389.

FIELD OF THE INVENTION

The present invention relates to apparatus, systems and methods for facilitating distribution of bicarbonate concentrate for use in hemodialysis. More particularly, the present invention relates to a centralized bicarbonate concentrate circulatory system for automatically controlled distribution and recirculation of bicarbonate concentrate to service a plurality of remote hemodialysis stations while achieving necessary control of various bicarbonate concentrate characteristics, including concentration, acidity and temperature, as well as the degree of contaminants.

BACKGROUND OF THE INVENTION

Over the last decade, bicarbonate dialysates have become increasingly significant for use in hemodialysis. The most common of previous dialysates were based on acetic acid, which inherently provided a very stable, bacteria-static solution which could be handled and processed with relatively little concern over bacterial contamination or fluctuating pH levels. Despite how stable the acetate dialysates were, though, the hemodialysis patients who underwent their treatment were not—it was quite common with acetate dialysates for patients to become nauseous and otherwise discomforted. Bicarbonate dialysates (i.e., dialysates having a bicarbonate base) were found to drastically reduce such patient discomfort and, consequently, most hemodialytic processes today employ bicarbonate dialysates.

Regardless of the type of dialysate, the preparation and delivery of solutions for use in dialysis has ordinarily been performed on a batch-by-batch basis, with the dialysate being prepared at the particular dialysis machine immediately prior to use. Such on-site preparation enables variation in the prescription of the dialysate from one patient to the next, which has become increasingly common. At the sacrifice of such flexibility, it has also been common to mix and test dialysates at a central location and then deliver it in separately sealed bottles to separate hemodialysis stations for prompt usage. In either case, the burdens of manual delivery, mixing, and the continuous need to replenish the bottles of dialysate solutions are readily appreciated by hospital technicians and others attending to such tasks and, as a consequence, to those responsible for administering hemodialysis services.

To alleviate analogous problems in other fields of dialysis, the mixing and distribution of dialysates has been relatively centralized and automated in some instances by supplying a pre-mixed dialysate through separate conduits from a bulk reservoir. Systems employing centralized peritoneal dialysate distribution, for example, have been referenced in McDonald, Harold, Jr., "Replacement of Renal Function", *European Dialysis and Transplant Association*, Vol. III, 1966, at pages 366-367. Other types of non-centralized but automated systems have also been known in the field of peritoneal dialysis, such as may be further evidenced in McDonald, Harold P., Jr., "An Automatic Peritoneal Dialysis Machine: Preliminary Report", *Transamerican Society for Artificial Internal Organs*, Vol XI, 1965, at pages 83-85. Such centralized systems, in theory, should provide for greater economies and greater time efficiencies in almost any large-scale system, but they are simply unworkable for centralized distribution of bicarbonate concentrate. In short, despite how elementary the general concept of centralized and/or automated bicarbonate concentrate delivery may be, the practical distribution of bicarbonate concentrates through such systems while maintaining required performance and safety standards has been extremely elusive.

Among the most critical of the difficulties which must be overcome to realize centralized distribution of bicarbonate concentrates relates to the inability to adequately control the acidity of bicarbonate concentrates and reduce micro-contamination thereof. The hydrostatic pressure required for a central distribution system having multiple outlets tends to produce greater flow velocities which, in turn, increase aeration of centrally-distributed bicarbonate concentrate. Turbulence created in mixing and circulating the bicarbonate concentrate also tends to increase aeration. Unfortunately, bicarbonate concentrates used in hemodialysis are especially susceptible to deterioration when aerated. Specifically, when bicarbonate concentrate is aerated, the $CO_2$ of bicarbonate tends to be liberated by aeration of the bicarbonate and, consequently, the pH of the bicarbonate concentrate fluctuates drastically. Due in part to such bicarbonate concentrate deterioration, centralized distribution systems have long been unsuccessful for distributing bicarbonate concentrates.

One example of the costly failures of others in this field occurred several years ago in a Kansas City facility. In that case, a centralized bicarbonate bicarbonate concentrate distribution system was constructed with the goal of servicing multiple hemodialysis patients. Regretably, the system failed and the centralized aspects of the Kansas City facility had to be abandoned due to the inability to control the pH and micro-contamination of the bicarbonate concentrate—naturally at a great loss to the hospital. Other attempts over the years have similarly failed and, consequently, the medical community has confirmed, re-confirmed, and finally conceded that such centralized bicarbonate concentrate distribution systems are simply unworkable on a practical basis.

Therefore and for still other reasons which will be apparent, it is an object of the present invention to provide a centralized bicarbonate distribution system which is capable of accommodating numerous stations without detrimental aeration of the bicarbonate. Another object is to provide for such distribution of the bicarbonate in a concentrate form so that it can be mixed with other ingredients according to varying prescriptions at different dialysis stations.

A countervailing consideration is the retarding of bacterial growth in the conduits of a centralized distribution system. To alleviate this problem in the field of peritoneal dialysis, centralized dyalisate distribution systems have been constructed wherein independent bicarbonate concentrate lines are selectively employed to service single peritoneal dialysis stations and, following such service, all the in-line bicarbonate concentrate is expelled through a drainage system as waste.

It is also a primary object of the present invention to minimize or prevent bacterial growth within systems constructed according to other objects of the invention, which includes preventing bacterial growth in the bicarbonate concentrates commonly employed today. Another object of the present invention is to enable centralized distribution of bicarbonate concentrate in a system which recirculates the bicarbonate concentrate from remote stations while also addressing other objects of the present invention.

Existing dialysis machines are limited to the extent of the pressure which they are capable of sustaining under normal operation. This is primarily due to the fact that they are designed to operate by drawing bicarbonate concentrate from a pre-mixed bottle, rather than a pressurized source. It has been found by Applicant that providing a line pressure greater than 15 p.s.i. tends to affect the dialysis operation in such conventional dialysis machines. Therefore, to accommodate presently available dialysis equipment, it is yet another object of the present invention to distribute diaylsate to multiple stations having conventional dialysis machines in a manner such that the bicarbonate concentrate is introduced to such machines at pressure levels which do not inhibit their operation. A related object of the present invention is to provide a centralized bicarbonate concentrate circulatory system for multiple stations which balances the object of maintaining bicarbonate concentrate pressures at operational levels for conventional dialysis machines while simultaneously addressing the other objects of the invention, including the objects of minimizing bacterial growth and controlling the pH and contaminant concentrations of the bicarbonate concentrate.

Moreover, it is an object of the present invention to provide a self-sterilizing bicarbonate distribution system or one which is capable of continual operation despite intermittent sterilization.

It is also an object of the present invention to enable achievement of all applicable hemodialysis standards in a centralized bicarbonate concentrate distribution system. Such standards have been emperically established by the medical community in general. Many of such standards are embodied in the *AAMI* 1982 Standards for Hemodialysis Systems published by the American Association of Medical Instrumentation (which are incorporated herein by this reference), and other standards of good workmanship known to those in the fields of the present invention.

Underlying each of the objects of the invention is the fundamental and pervasive object of providing better and perhaps more economical service to dialysis patients by overcoming the problems and deficiencies of the prior art. More particularly, it is an object of the present invention to provide a new and improved centralized bicarbonate concentrate distribution system and related methods for use in facilitating dialysis. Many other problems, obstacles and deficiencies faced by the prior art and addressed by the present invention will be obvious to those skilled in that art, especially in light of the description herein.

SUMMARY OF THE INVENTION

The present invention is directed to accomplishing such objects and obvious others by providing a centralized bicarbonate concentrate distribution system which minimizes bacterial contamination and which ensures a stable pH level. Such a system may, more particularly include a holding tank for containing bicarbonate concentrate, a distribution line for conducting bicarbonate concentrate from said tank to the separate proximities of a plurality of dialysis stations at which said bicarbonate concentrate is selectively divertable from said distribution line for dialytic use, and a pump which is operated in conjunction with various valves and in coordination with the characteristics of the distribution line to maintain continuous flow of the bicarbonate concentrate through the distribution line in a recirculating manner despite varying demands for the dialysis.

The distribution line is connected at a first end to an outlet of said tank and related components and at a second end to an inlet of said tank to complete a circuit through which the concentrate may be continuously and steadily recirculated. The distribution line is actually directed through two parallel circuits to within the said proximities of the remote stations with a series of six-inch stems allowing for divertion of the concentrate while minimizing stagnation.

The centralized bicarbonate concentrate distribution system may also include a control valve positioned downstream of the remote stations for maintaining the flow rate of bicarbonate concentrate between five and ten feet per second throughout said distribution line while simultaneously maintaining predominately laminar flow. The system is further adapted to maintain the pressure in said distribution line at or less than or equal to fifteen (15) p.s.i. at each of the remote stations, and the distribution line is sized to accomodate the operation of the control valve to further ensure such flow characteristics.

Other features which will be described more fully relate to a concentrate tank which minimizes turbulence, and related features including a level control for maintaining the level of bicarbonate concentrate within said tank above a certain minimum level, and an inlet of said tank formed by a diffusion lateral which is constructed in a manner such that said bicarbonate concentrate is introduced into a body of bicarbonate concentrate contained in said tank at a level beneath said certain minimum level.

Systems of the invention also monitor other characteristics of the bicarbonate system including concentration and pressure levels while providing controls for such when operating with poor unacceptable characteristics.

Many other objects, features and advantages of the invention will be obvious to those of skill in the art in light of this application.

Hereafter, presently preferred embodiments constructed according to the teachings of the present invention are described in more detail. To those of ordinary skill in the art, the invention will become more readily understood from the specifications of those embodiments, particularly when considered in light of the appended claims and with reference to the accompanying drawings, wherein like numerals refer to like elements throughout, and wherein:

DETAILED DESCRIPTION OF THE PREFERRED EMBODIMENT

Figure 1:
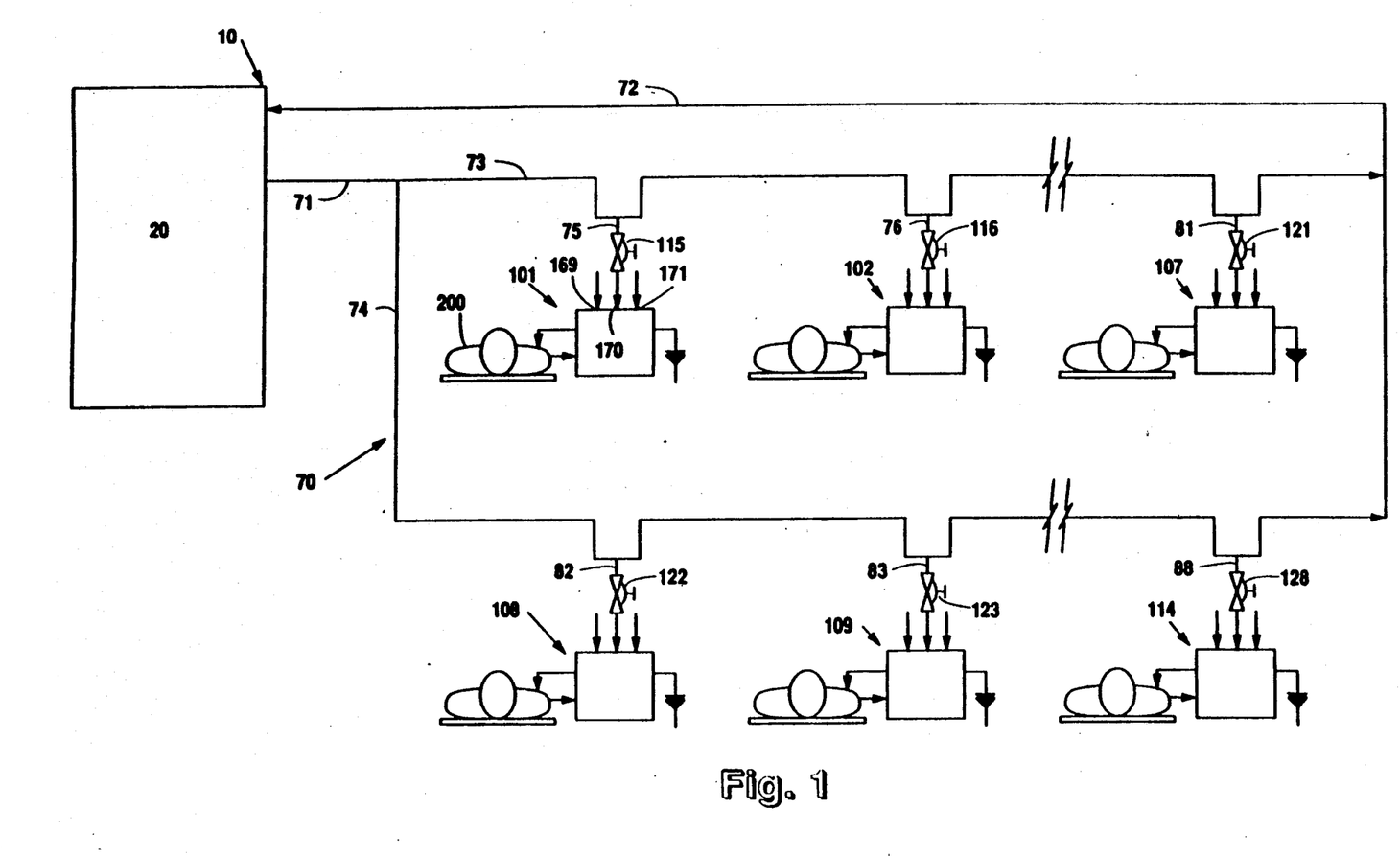
FIG. 1 shows a centralized bicarbonate concentrate distribution system 10 constructed according to the teachings of the present invention.

Referring to FIG. 1, many aspects of the present invention may be embodied in the form of a centralized bicarbonate concentrate distribution system 10 which is a preferred embodiment of the invention. The system 10, more particularly, comprises a bicarbonate concentrate control and processing unit 20 in combination with a distribution line 70 for distributing bicarbonate concentrate to a plurality of dialysis stations 101-114 (stations 103-106 and 110-113 being omitted from the drawings to simplify the same).

In the preferred embodiment, the dialysis stations 101-114, themselves, are standard dialysis machines for conducting hemodialysis, which may also be referred to as "renal dialysis". For simplicity in this description, each of stations 101-114 are identical, although it should be understood that varying types of stations could be serviced by system 10. Referring specifically to station 101 as representative of each of stations 101-114, station 101 is conventionally adapted for performing hemodialysis on a patient 200 using a dialysate formed from the combination of a plurality of solutions according to a given prescription. In the preferred embodiment, those solutions are purified water, concentrated acetate, and of course bicarbonate concentrate, although various other constituents may also be desirable as will be known or obvious to those of ordinary skill in the art of dialysis. Those solutions are separately introduced into station 101 through inlets 169-171, with the bicarbonate concentrate being introduced through inlet 170 when valve 115 is opened.

As will be apparent to those in the art, the present invention is extremely significant due in part to the fact that it enables ready supply of bicarbonate concentrate which is so susceptible to deterioration, contamination and drastic pH swings. However, as will also be apparent to such individuals, many aspects of the present invention will be equally applicable for distribution of more stable dialysate solutions such as pre-mixed bicarbonate dialysates or acetate dialysates. In fact, in the preferred embodiment of the present invention, centralized distribution systems which mirror the system 10 are also provided for distribution of the purified water and the acetate concentrate to inlets 169 and 171 of each of stations 101-114. Such centralized distribution systems for the other solutions are constructed in a manner similar to the system 10, although manual pouring and other known or obvious systems can also be used in conjunction with system 10.

Focusing on the bicarbonate concentrate distribution system 10, system 10 generally functions to provide a steady flow of bicarbonate concentrate to the remote proximities of each of the dialysis stations 101-114, even though the operation of the stations 101-114 may be intermitent or have fluctuating demands. Such a system 10 is ideal for employment in hospital environments and the like wherein the number of patients requiring dialysis fluctuates. To accomodate the fluctuating demands of such stations, the system 10 is adapted according to the present invention to provide a continual, relatively steady bicarbonate concentrate flow through distribution line 70 regardless whether all or none of the stations 101-114 are currently in operation. When required by individual ones of stations 101-114, portions of the flow of bicarbonate concentrate are selectively divertable from distribution line 70 through pipe stems 75-88 by appropriate opening of valves 115-128, respectively. Incidentally, although the preferred embodiment is actually adapted to service fourteen remote stations 101-114, it is conceived that many more could also be serviced.

By means which will be described more fully herein, the system 10 is particularly adapted to maintain the flow of the bicarbonate concentrate through distribution line 70 with predominantly laminar flow characteristics throughout. Additionally, various features of the system 10 (including the sizing of distribution line 70) cooperate to ensure that the flow rate of the bicarbonate concentrate in distribution line 70 is maintained throughout line 70 at approximately seven (7) feet per second while the pressure at each of stations 101-114 is maintained at less than 15 p.s.i. for each of such stations, despite the varying demands on the system 10.

Figure 2:
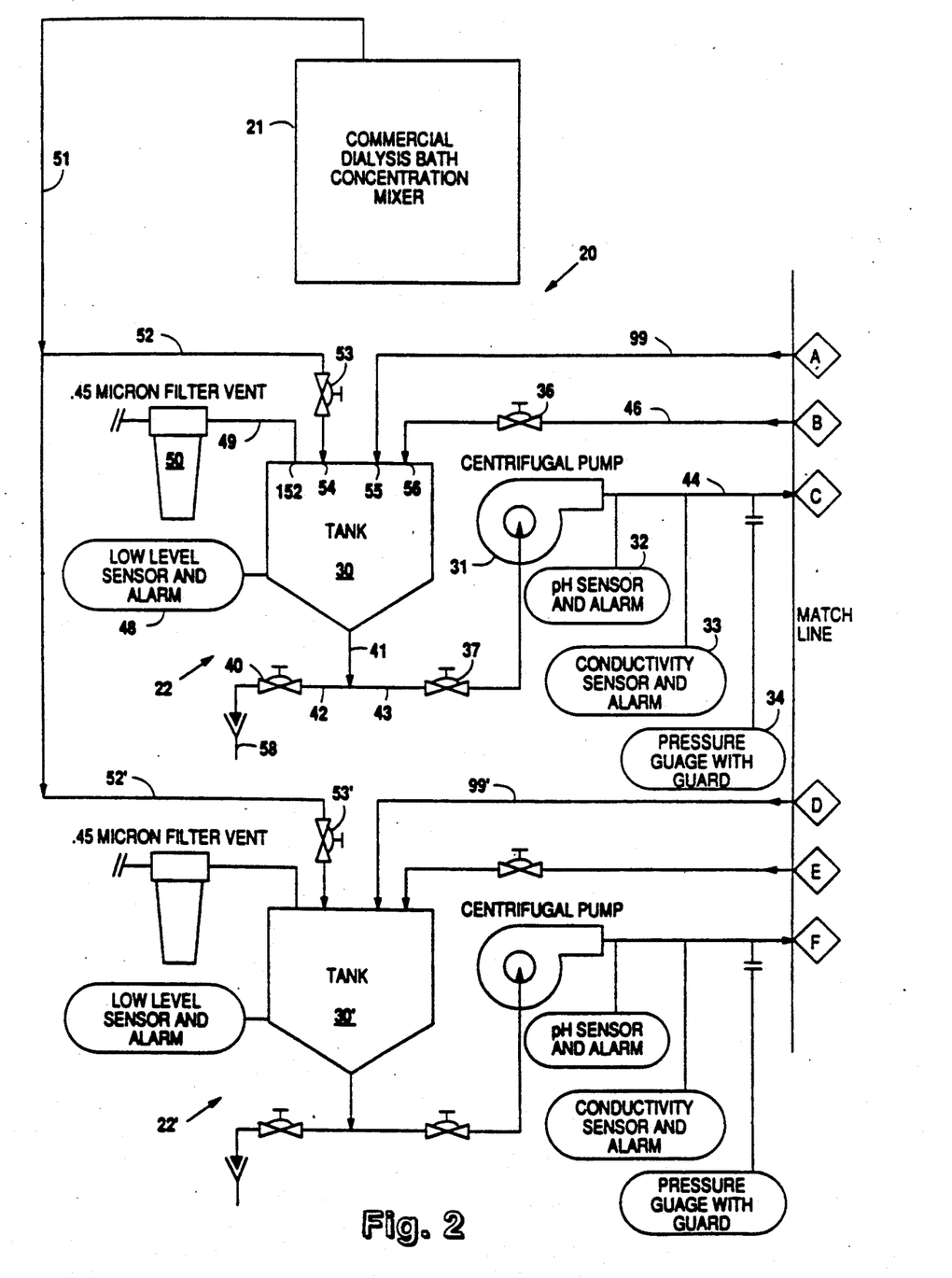
FIGS. 2 and 3, viewed in conjunction with one another, show more detailed features of the bicarbonate concentrate control and processing unit 20 which is a major component of the centralized system 10 shown in FIG. 1.
Figure 3:
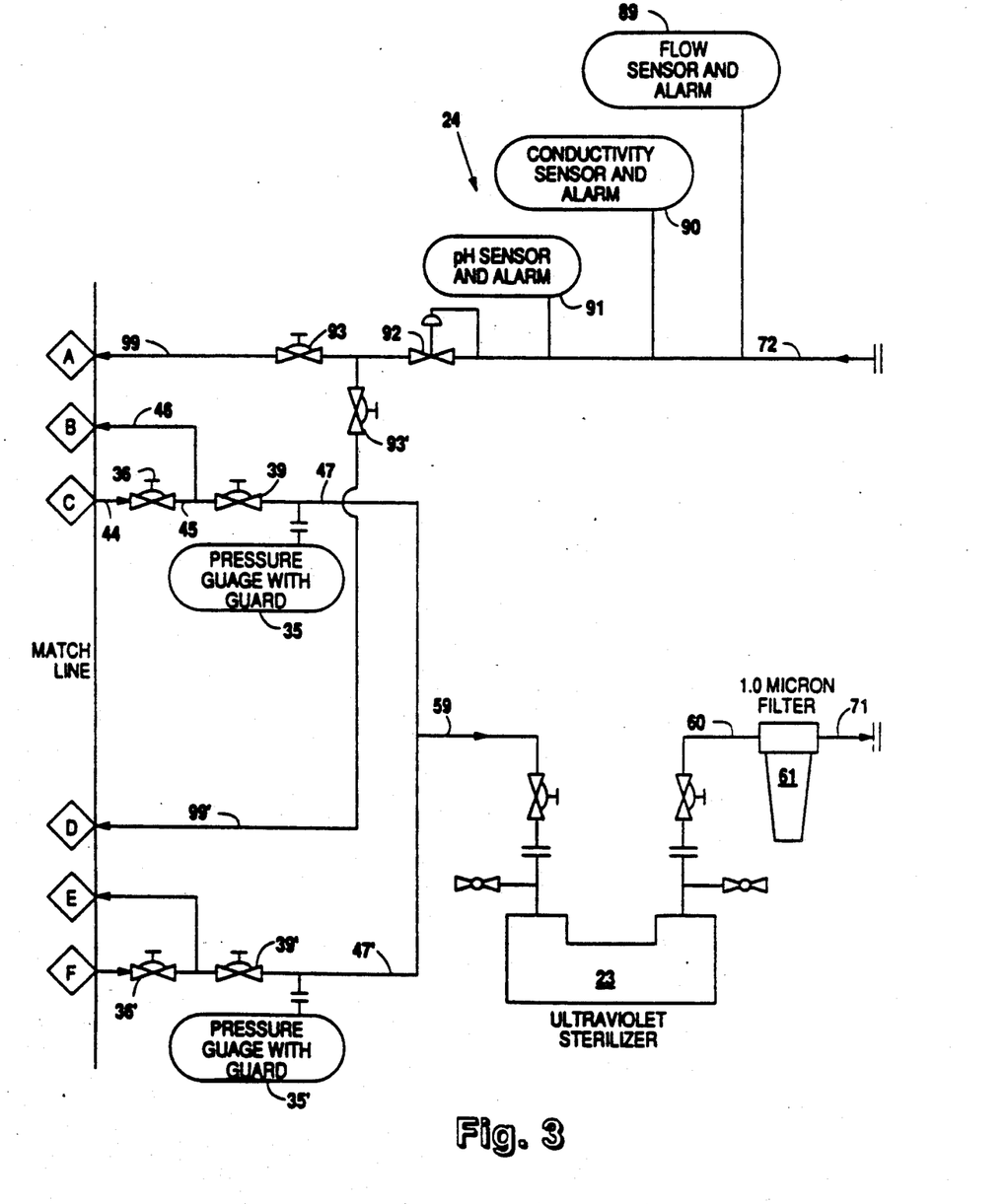

Referring to FIGS. 2 and 3 in conjunction with one another by matching points A-F on each, the bicarbonate concentrate control and processing unit 20 is shown in more detail. Unit 20 basically comprises a commercial dialysis bath concentration mixer 21, a first recirculating sub-system 22, a second recirculating sub-system 22', an ultraviolet sterilizer 23, overall system controls and alarms 24, along with various conduits and valves interconnecting each of said components 21-24 into a functioning whole.

Subsystem 22 basically includes a bicarbonate concentrate tank 30, a centrifugal pump 31, pH sensor and alarm 32, conductivity sensor and alarm 33, pressure gauges 34 and 35, valves 36-40 and connecting conduits 41-47. Additionally, bicarbonate concentrate tank 30 is provided with a low level sensor and alarm 48 and a vent line 49 having a 0.45 micron filter 50 therein.

Subsystem 22' is provided in addition to subsystem 22 to fulfill a couple of basic purposes. Simply put, subsystem 22' is primarily provided to enable continuous operation of the system 10 by providing a backup for subsystem 22. The backup of subsystem 22' is critical not only in the event of a failure of one of subsystem 22 but, more frequently, for enabling routine sterilizing of subsystems 22 and 22'. By including a back-up sub-system, the operation of one of said substances 22 and 22' can be temporarily interrupted so that the other of said subsystems 22, 22' can be flushed and sterilized. Valves 39, 93 and others facilitate such temporary shutdown and sterilization as will be clear to those of ordinary skill in the art. Recirculating subsystems 22 and 22' are identical in the preferred embodiment and, therefore and for simplicity, description of sub-system 22 is submitted to be descriptive of both subsystems 22 and 22'. At various other points in this description, though, description or reference to the reference numerals for specific components of the subsystem 22' is made with the same designations as the similar components of subsystem 22, except that the components of subsystem 22' are followed with a prime (" ' ") designation.

Each of subsystems 22 and 22' are provided with fresh bicarbonate concentrate from a commercial dialysis bath concentration mixer 21. The mixer 21 is a standardly available mixer produced by Renal Systems for preparing fresh bicarbonate concentrate. The bicarbonate concentrate, itself, is a combination of bicarbonate powder and purified water. Once mixed by mixer 21, the fresh bicarbonate concentrate is distributed to subsystems 22 and 22' by way of a bicarbonate concentrate conduit 51 which branches into conduits 52 and 52' directed to subsystems 22 and 22', respectively. The proportion of the bicarbonate concentrate conveyed to subsystem 22 relative to subsystem 22' is dictated by the ratio of the adjustments between fresh bicarbonate concentrate valves 53 and 53'.

The fresh bicarbonate concentrate introduced into subsystems 22 and 22' according to the adjustment of valves 53 and 53' in lines 52 and 52' is typically mixed in tanks 30 and 30' with bicarbonate concentrate that has been previously and continuously circulated through distribution line 70 (shown in FIG. 1). In total, tank 30 has three inlets 54–56 (described further herein) while tank 30 has a single outlet 57. From tank 30, bicarbonate concentrate flows due to hydrostatic pressure through stem 41 to branch conduits 42 and 43 which lead to a drain 58 and centrifugal pump 31, respectively. The flows through branch conduits 42 and 43 are controlled by valves 40 and 37, respectively. From branch conduit 43, centrifugal pump 31 pumps the bicarbonate concentrate to provide for circulation thereof—either within subsystem 22 or throughout the entire system 10, depending on the adjustment of valves 38 and 39. According to their functions, valve 38 is referred to as "mixing valve" for mixing within subsystem 22 to maintain the flow therein and valve 29 opening the flow of bicarbonate concentrate within subsystem 22 to the entire system 10.

From subsystems 22 and 22', the bicarbonate concentrate is directed, according to the adjustment of valves 39 and 39', respectively, through conduit 59 to ultraviolet sterilizer 23. Ultraviolet sterilizer 23 is a standard sterilizer used in bicarbonate concentrate processing for bathing the diaylsate in ultraviolet rays which tend to rupture bacteria into pyrogens which are then filtered out by 1.0 micron filter 61. More particularly, the bicarbonate concentrate is introduced through conduit 59 and through sterilizer 23 into conduit 60 which includes filter 61. From filter 61, the sterilized bicarbonate concentrate is distributed to stations 101–114 by way of distribution line 70. For maintenance purposes, sterilizer 23 is separable from conduits 59 and 60, although the details of this is not essential to the invention.

Subsystem 22 is also provided with a pump means 31 for circulating bicarbonate concentrate through distribution line 70. The pump means 31, particularly, is a centrifugal pump which produces an outflow of bicarbonate concentrate in conduit 44 which, in the preferred embodiment is predominantly laminar within conduit 44. Pump means 31 is a pump capable of producing a 20 p.s.i. pressure head in line 44.

Subsystem 22 also includes a ph sensor and alarm 32, a conductivity sensor and alarm 33, and a pressure gauge 34, each of which is tapped into conduit 44 in series downstream of centrifugal pump 31. The pH sensor 32 provides a means for monitoring the acidity of bicarbonate concentrate produced by subsystem 22, and conductivity sensor 33 provides a means for monitoring the concentration of bicarbonate concentrate produced by sub-system 22. The alarms of each of pH sensor 32 and conductivity sensor 33 are provided to initiate a warning signal when the pH or conductivity in line 44 falls outside of predetermined perameters for the bicarbonate concentrate in line 44. Pressure gauge 34 enables monitoring of the pressure in line 44 to insure that the pressure of the bicarbonate concentrate pumped from centrifugal pump 31 does not cause the pressures either within subsystem 22 or in distribution line 70 to exceed the maximum operational pressures. A second pressure gauge 35 is positioned downstream of valve 39 to more accurately monitor the pressure of bicarbonate concentrate which finally exits from subsystem 22 and is directed into distribution line 70. Each of pressure gauges 34 and 35 are provided with a guard for relieving pressure in conduits 44 and 47, respectively, when such pressures exceed the predetermined maximum operating levels in each.

Similarly, the overall system 10 is provided with various controls and alarms 24 in return conduit 72 for monitoring the bicarbonate concentrate returned from distribution line 70. More particularly, a flow sensor and alarm 89, a conductivity sensor and alarm 90, and a pH sensor and alarm 91 are provided to monitor corresponding properties of the bicarbonate concentrate in the return conduit 72. Additionally, a control valve 92 is provided as a primary means for controlling the flow rate of bicarbonate concentrate throughout distribution line 70. Valve 92 is controlled by computer according to the properties of the flow in conduit 72. Thus, much like the thumb at the end of a garden hose is capable of controlling the pressure and flow rate within the hose, valve 92 is capable of controlling the flow rate in distribution line 70.

Referring again to FIG. 1, distribution line 70 distributes bicarbonate concentrate from unit 20 to the proximity of a plurality of remote dialysis stations 101–114. More particularly, the bicarbonate concentrate is directed from unit 20 through conduit 71 and into two branches 73 and 74 of distribution line 70. Each of the branches 73 and 74 services a separate series (or "circuit") of dialysis stations—branch 73 servicing stations 101–107, and branch 74 servicing stations 108–114.

As previously mentioned, the flow rate throughout the distribution line 70 is maintained at approximately seven feet per second which, depending on the number of stations per circuit that are currently in operation, can vary anywhere between five and ten feet per second at different portions of distribution line 70. Nevertheless, as long as the rate is maintained within that range of velocities (i.e., at approximately seven feed per second) Applicant has found that laminar flow can be maintained at pressures less than 15 p.s.i. while still adequately servicing each of the stations 101–114. The control of the flow rate throughout distribution line 70 is not only affectuated by means of control valves 92 but also by appropriate sizing of the branches 73 and 74. More specifically, in the preferred embodiment, Applicant has found that a gradual reduction in diameter in each of branches 73 and 74 from ¾ inch conduit to ½ inch inside diameter conduit facilitates the pressure and velocity control of the flow of bicarbonate concentrate through branches 73 and 74 despite the fluctuating demands for each.

Thus, in operation, bicarbonate concentrate flow through the entire distribution line 70 can be continually maintained at approximately seven feet per second and at less than or equal to 15 p.s.i. despite the fluctuating demands by stations 101–114. In addition, due to the previously described features of subsystems 22 and 22', circulation within either or both of subsystems 22 or 22' can be equally maintained even if the flow demands on distribution line 70 are minimized to nothing. More particularly, to accomodate such minimal demands, when subsystem 22 is providing the bicarbonate concentrate flow, valves 36, 38, 39 and 92 are cooperatively adjusted to maintain the proper flow rate in distribution lines 70 by diverting a portion of the flow in conduit 44 through conduit 46 in a mixing fashion back into tank 30 without having been directed through distribution line 70.

Ordinarilly, valves 39 and 39' are adjusted such that only one of subsystems 22 and 22' is providing bicarbonate concentrate for distribution through distribution line 70. However, during periods of peak demands, both of subsystems 22 and 22' are opened in communication with distribution line 70 to accomodate the greater demands. When either of subsystems 22 or 22' is shut off from distribution line 70 by means of valves 39 and 39' respectively, the appropriate valve 36 or 36' is adjusted to provide free mixing of the bicarbonate concentrate within the respective subsystem 22, 22' in an internal circuit consisting basically from tank 30 through conduits 41, 43, 45 and 46 back to tank 30. In addition to the adjustment of valves 39 and 39', valves 93 and 93' are adjusted to appropriately divert the return flow of bicarbonate concentrate from line 72 to the fully operational subsystem 22 or 22'.

Each of valves 36–40, 36'–40', 53, 53', 92, 93, 93' and 115-128 are conventional, variable-flow diaphram valves which help to minimize bacterial growth within system 10 by minimizing discontinuities in which bacteria may grow and by minimizing the opportunity for bacteria to enter system 10. As for the conduits themselves, specifically conduits 41–47, 51, 52, 71-88, 41'–47', and 52', each of such may be any appropriate conduit for conducting bicarbonate concentrate liquid. In the preferred embodiment, such conduits are PVC pipe which are sized and configured in accordance with the other aspects of system 10, particularly in order to achieve the flow characteristics described elsewhere herein.

Figure 4:
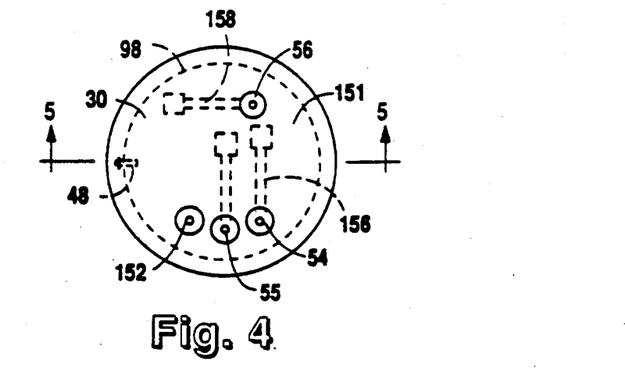
FIG. 4 shows a top view of the bicarbonate concentrate tank 30 of the bicarbonate concentrate control and processing unit 20 of the preferred embodiment.
Figure 5:
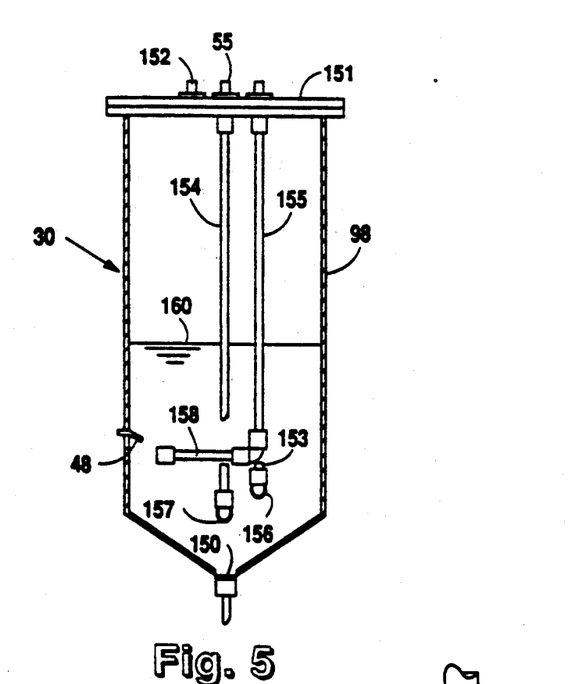
FIG. 5 shows a partially-sectioned and partially broken-away elevation view of the bicarbonate concentrate tank 30 of FIG. 4 and related components, wherein the walls 98 of tank 30 are shown sagitally sectioned along sectional plane 5—5 of FIG. 4.
Figure 6:
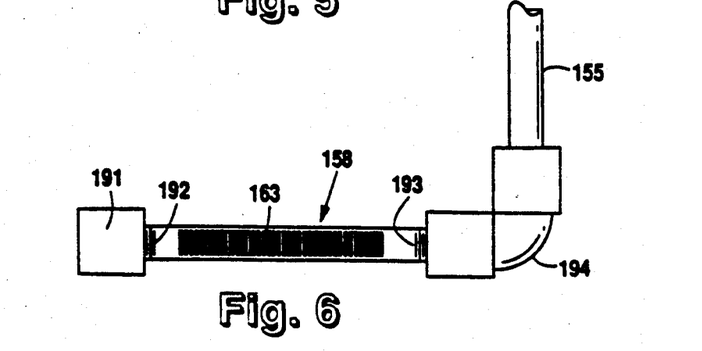
FIG. 6 shows a detailed view of the lateral 97 shown in FIG. 5.

Referring to FIGS. 4–6, tank 30 and its entrails are shown in more detail. Tank 30 basically is a conventional bicarbonate concentrate tank in the sense that it is a sealed container having a funnel-shaped outlet in the lower portion thereof for delivering bicarbonate concentrate under the influence of gravity through that outlet 150. As also mentioned, and with particular reference to FIG. 4, tank 30 has three inlets 54–56. Inlet 54 is the fill inlet for introducing fresh bicarbonate concentrate into tank 30 from the branch conduit 52 when valve 53 is appropriately opened.

A second inlet, inlet 55, is the mixing inlet for use during internal circulation with subsystem 22 when flow from pump 31 is diverted through line 46 by adjustment of valves 36, 38 and 39. The remaining inlet, inlet 56 is a return inlet for directing bicarbonate concentrate from return line 72 into tank 30 for recirculation through distribution line 70. As will be apparent to those of ordinary skill in the art, the flow rates into inlets 54–56 will vary depending on the particular stage of operation of system 10; however, generally speaking the greatest flow rate of inflowing bicarbonate concentrate is introduced through mixing inlet 55 due to the relatively short circuit that is effectuated during mixing cycles of subsystem 22. A top plate 151 of tank 30 is sealed around its perimeter to form the top of tank 30 and four holes are drilled therein to provide inlets 54–56 and vent hole 152. Referring to FIG. 2, vent hole 152 is connected to a ventilation conduit 49 (also PVC pipe) having a 0.45 micron filter 50 connected therein for filtering impurities from the gases which are directed therethrough. The purpose of vent hole 152 is to equalize the pressure within tank 30 despite fluctuating levels of the bicarbonate concentrate therein.

Referring particularly to FIG. 5, the intrails of tank 30 include 3 vertical conduits 153-155 which are separately sealed to the respective inlets 54–56 for conducting bicarbonate concentrate from said inlets 54–56 to a depth beneath the upper level of the bicarbonate concentrate in the bottom of tank 30. The level of bicarbonate concentrate within tank 30 is ensured to be above a certain minimum level of means of a low level sensor 48. Low level sensor 48 is a float actuated switch having electrical output linked with an alarm system for initiating a warning signal when the level 160 of bicarbonate concentrate within tank 30 drops beneath the elevation of low level sensor 48. Each of the inlet conduit 153-155 has portal means located at an elevation sufficiently beneath the elevation of low level sensor 48 such that aeration is minimized during the introduction of bicarbonate concentrate into tank 30. For further minimizing such aeration, laterals 156-158 are connected to the portal ends of inlet conduits 153-155, respectively. Lateral conduits 156-158 actually define the portal means through which the bicarbonate concentrate enters tank 30 from inlets 54–56, respectively.

Referring to FIG. 6, which shows the detail of lateral 158, each of laterals 156-158 is a horizontally disposed section of pipe with a cap 191 on the distal end 192 thereof. Each of laterals 156-158 are identical. Cap 191 seals the end 192 of the lateral conduit 158 while the proximal end 193 of the conduit 156 is joined to the vertical conduit 155 by means of a rounded elbow 194. Additionally, on each lateral side of lateral 158, a series of vertical slits 163 are provided as means of diffusing the introduction of bicarbonate concentrate from the corresponding fill inlet 54 into the liquid bicarbonate concentrate already contained in tank 30. Thus, by diffusing the entry of bicarbonate concentrate into tank 30, turbulance in that bicarbonate concentrate is minimized to an unappreciable amount, which further minimizes the possibilities of aeration of the bicarbonate concentrate, thereby prolonging the effective life of the bicarbonate concentrate.

Though described in terms of the foregoing preferred embodiments, such embodiments are merely exemplary of the present invention. In addition many other alternatives, variations, adaptations, modifications, equivalents and substitutions are anticipated and intended. For instance, although many aspects of the present invention are limited to hemodialysis and, particularly, bicarbonate dialysis, it is conceived that several other disclosed aspects of the invention are equally applicable in the field of peritoneal dialysis, as will be obvious to those of ordinary skill in that field of the art.

I claim:

1. A system comprising centralized bicarbonate concentrate distribution system, for servicing a plurality of dialysis stations while minimizing detrimental aeration of said bicarbonate, including:
    a holding tank for containing bicarbonate concentrate;
    a distribution line connected at a first end to an outlet of said tank and at a second end to an inlet of said tank, said distribution line being directed from said tank through a circuit for conducting bicarbonate concentrate from said tank to the separate proximities of a plurality of dialysis stations at which said bicarbonate concentrate is selectively divertable from said distribution line for use in dialysis at the respective stations; and means for maintaining continuous flow of said bicarbonate concentrate through said distribution line in a recirculating manner despite varying demands for the dialysis.

2. The centralized bicarbonate concentrate distribution system of claim 1, further comprising:

a control valve for maintaining the flow rate of bicarbonate concentrate between five and ten feet per second throughout said distribution line; and wherein said distribution line is sized to accomodate the operation of said control valve.

3. The system of claim 2 wherein said flow maintaining means is further adapted to maintain the pressure in said distribution line at or less than or equal to fifteen (15) p.s.i. at each of said proximities.

4. The system of claim 2 wherein said control valve is positioned in said distribution line downstream from each of said separate proximities.

5. The system of claim 1, further comprising;

a level control for maintaining the level of bicarbonate concentrate within said tank above a certain minimum level; and the second end of said distribution line is connected to an inlet of said tank in a manner such that said bicarbonate concentrate is introduced into a body of bicarbonate concentrate contained in said tank at a level beneath said certain minimum level.

6. The system of the claim 5, further comprising;

a lateral conduit positioned within said tank beneath said certain minimum level and connected in fluid communication with said inlet in a manner such that said bicarbonate concentrate is conducted through portal means of said lateral conduit for introduction into said body of bicarbonate concentrate contained in said tank.

7. The system of claim 6 wherein:

said portal means is provided with diffusion means for diffusing the flow of said bicarbonate concentrate through said portal means to reduce turbulence within said body of bicarbonate concentrate contained in said tank.

8. The system of claim 7 wherein:

said diffusion means is provided by a plurality of slots formed in the wall of said lateral conduit, said slots being perpendicular to length of said lateral conduit.

9. The system of claim 8 wherein:

the rate of said flow through said distribution line is balanced with the pressure of said bicarbonate concentrate by means of a control valve in said distribution line, said control valve being variably adjustable between a first open position and a second closed position.

* * * * *